United States Patent
Beller et al.

(10) Patent No.: US 8,449,318 B2
(45) Date of Patent: May 28, 2013

(54) PLUG SYSTEM FOR SURGICAL DEVICES

(75) Inventors: Jürgen Beller, Gomaringen (DE); Florian Eisele, Freiburg (DE)

(73) Assignee: Erbe Elektromedizin GmbH, Tübingen (DE)

( * ) Notice: Subject to any disclaimer, the term of this patent is extended or adjusted under 35 U.S.C. 154(b) by 176 days.

(21) Appl. No.: 12/809,033

(22) PCT Filed: Dec. 11, 2008

(86) PCT No.: PCT/EP2008/010555
§ 371 (c)(1),
(2), (4) Date: Nov. 4, 2010

(87) PCT Pub. No.: WO2009/080221
PCT Pub. Date: Jul. 2, 2009

(65) Prior Publication Data
US 2011/0045680 A1   Feb. 24, 2011

(30) Foreign Application Priority Data
Dec. 20, 2007 (DE) .......................... 10 2007 061 483

(51) Int. Cl.
*H01R 13/00* (2006.01)
(52) U.S. Cl.
USPC .......................................... 439/489; 439/955
(58) Field of Classification Search
CPC ........................................................ H01R 29/00
USPC .............................. 439/489, 188, 955; 604/34
See application file for complete search history.

(56) References Cited

U.S. PATENT DOCUMENTS

| | | | | |
|---|---|---|---|---|
| 4,407,298 A * | 10/1983 | Lentz et al. | .................... | 600/526 |
| 4,450,487 A * | 5/1984 | Koide | ............................ | 386/200 |
| 4,571,488 A * | 2/1986 | Reeves | .......................... | 219/544 |
| 4,611,601 A * | 9/1986 | Bowman | ....................... | 600/486 |
| 4,811,740 A * | 3/1989 | Ikeda et al. | ..................... | 600/437 |
| 4,915,639 A * | 4/1990 | Cohn et al. | .................... | 439/188 |
| 4,924,520 A * | 5/1990 | Kolbert | ........................... | 380/59 |
| 5,169,328 A * | 12/1992 | Johnson | .......................... | 439/188 |
| 5,181,858 A * | 1/1993 | Matz et al. | ..................... | 439/188 |
| 5,209,235 A * | 5/1993 | Brisken et al. | ................ | 600/466 |
| 5,222,164 A * | 6/1993 | Bass et al. | ........................ | 385/14 |
| 5,274,319 A * | 12/1993 | Keener et al. | ................. | 320/106 |

(Continued)

FOREIGN PATENT DOCUMENTS

| DE | 1 075 235 B | 8/1960 |
|---|---|---|
| DE | 102 53 819 A1 | 7/2004 |

(Continued)

*Primary Examiner* — Neil Abrams
(74) *Attorney, Agent, or Firm* — Dickstein Shapiro LLP

(57) ABSTRACT

A plug system for surgical devices includes a plurality of sockets into which connecting plugs of electrosurgical instruments can be inserted, and a switching matrix having a plurality of switches for connecting at least one of the sockets to at least two different outputs or inputs of an electrosurgery device. A control system having a preselection device for controlling the switching matrix is arranged in the plug system. The switching matrix connects predetermined sockets to predetermined inputs or outputs, depending on data input into the preselection device. The control system includes a storage element for storing a basic configuration of a connection between the sockets and the inputs or outputs of the electrosurgery device. The basic configuration is set if no data is entered into the preselection device, and all switches are open in the basic configuration.

12 Claims, 2 Drawing Sheets

U.S. PATENT DOCUMENTS

| | | | |
|---|---|---|---|
| 5,342,356 A * | 8/1994 | Ellman et al. ................... 606/32 |
| 5,347,113 A * | 9/1994 | Reddersen et al. ...... 235/462.15 |
| 5,357,076 A * | 10/1994 | Blankenship ............ 219/121.54 |
| 5,400,267 A * | 3/1995 | Denen et al. ..................... 702/59 |
| 5,405,269 A * | 4/1995 | Stupecky ...................... 439/191 |
| 5,423,873 A | 6/1995 | Neubauer et al. |
| 5,478,250 A * | 12/1995 | Hoffman ....................... 439/142 |
| 5,491,418 A * | 2/1996 | Alfaro et al. .................. 324/402 |
| 5,573,533 A | 11/1996 | Strul |
| 5,660,567 A * | 8/1997 | Nierlich et al. .......... 439/620.21 |
| 5,773,901 A * | 6/1998 | Kantner ........................ 307/125 |
| 5,822,427 A * | 10/1998 | Braitberg et al. ............. 379/454 |
| 5,865,546 A * | 2/1999 | Ganthier et al. .............. 400/489 |
| 5,934,610 A | 8/1999 | Karolys et al. ............... 244/53 R |
| 5,997,360 A * | 12/1999 | Gen-Kuong et al. ......... 439/700 |
| 6,044,700 A * | 4/2000 | Gen-Kuong et al. ....... 73/178 R |
| 6,068,627 A * | 5/2000 | Orszulak et al. ................ 606/34 |
| 6,074,386 A * | 6/2000 | Goble et al. .................... 606/34 |
| 6,113,596 A | 9/2000 | Hooven et al. |
| 6,126,610 A * | 10/2000 | Rich et al. ..................... 600/529 |
| 6,161,915 A * | 12/2000 | Bolash et al. ................... 347/19 |
| 6,402,743 B1 | 6/2002 | Orszulak et al. |
| 6,431,892 B1 * | 8/2002 | Shupe et al. .................. 439/188 |
| 6,452,402 B1 * | 9/2002 | Kerai ............................ 324/538 |
| 6,495,932 B1 * | 12/2002 | Yoshimizu et al. ........... 307/150 |
| 6,612,495 B2 * | 9/2003 | Reddersen et al. ...... 235/462.15 |
| 6,837,725 B1 * | 1/2005 | Gordon et al. ................ 439/188 |
| 6,913,477 B2 * | 7/2005 | Dayan et al. .................. 439/188 |
| 6,968,994 B1 * | 11/2005 | Ashwood Smith ........... 235/375 |
| 6,988,905 B2 * | 1/2006 | Corey et al. .................. 439/222 |
| 7,035,597 B2 * | 4/2006 | Maden ......................... 455/90.2 |
| 7,203,556 B2 * | 4/2007 | Daners ............................ 700/79 |
| 7,214,224 B2 * | 5/2007 | Goble .............................. 606/34 |
| 7,416,437 B2 * | 8/2008 | Sartor et al. .................. 439/489 |
| 7,444,936 B2 * | 11/2008 | Foley et al. ................... 101/484 |
| 7,493,437 B1 * | 2/2009 | Jones et al. ................... 710/301 |
| 7,589,536 B2 * | 9/2009 | Terlizzi et al. ............... 324/538 |
| 7,782,202 B2 * | 8/2010 | Downie et al. ............. 340/572.1 |
| 7,828,586 B2 * | 11/2010 | Gorczyca et al. ............ 439/489 |
| 8,029,313 B2 * | 10/2011 | Fendrock et al. ............ 439/489 |
| 8,107,243 B2 * | 1/2012 | Guccione et al. ............. 361/728 |
| 8,177,782 B2 * | 5/2012 | Beller et al. .................... 606/34 |
| 2003/0038177 A1 * | 2/2003 | Morrow ........................ 235/441 |
| 2003/0222503 A1 * | 12/2003 | Lam et al. ...................... 307/38 |
| 2004/0044339 A1 * | 3/2004 | Beller et al. .................... 606/34 |
| 2004/0054365 A1 | 3/2004 | Goble |
| 2005/0192609 A1 | 9/2005 | Whitman et al. |
| 2006/0200120 A1 | 9/2006 | DiCarlo et al. |
| 2006/0281360 A1 | 12/2006 | Sartor et al. |
| 2008/0114350 A1 * | 5/2008 | Park et al. ....................... 606/34 |
| 2008/0182442 A1 * | 7/2008 | Choi et al. .................... 439/166 |
| 2009/0190142 A1 * | 7/2009 | Taylor et al. ................... 358/1.1 |
| 2010/0191879 A1 * | 7/2010 | Pomerantz ...................... 710/73 |

FOREIGN PATENT DOCUMENTS

| | | |
|---|---|---|
| DE | 697 25 327 T2 | 8/2004 |
| DE | 10 2006 022606 A1 | 11/2007 |
| EP | 0 521 501 A2 | 1/1993 |
| EP | 0 819 409 A1 | 1/1998 |
| EP | 1 300 175 A2 | 4/2003 |
| WO | WO 2007/115655 A1 | 10/2007 |

* cited by examiner

US 8,449,318 B2

PLUG SYSTEM FOR SURGICAL DEVICES

FIELD OF THE INVENTION

Embodiments of the invention relate to a plug system for surgical devices.

BACKGROUND

In surgery, electrosurgery devices to which electrosurgical instruments can be connected are used. It is typical to connect different instruments to the same electrosurgery device or to connect the same instrument to different electrosurgery devices. Generally, the electrosurgical instruments can be connected to the electrosurgery device via electrical cables simultaneously or one after the other. The electrosurgery device generates electrical voltages or currents for monopolar, bipolar or multipolar cutting and/or coagulation of biological tissue by means of the electrosurgical instruments.

Typically, different surgical device plug systems are used to accommodate the connecting cables that are arranged between the electrosurgery device and the instrument. A large number of such plug systems have become available on the market.

To be able to connect the large number of electrosurgical instruments available on the market to the same electrosurgery device, various connecting sockets are provided, depending on the design of the electrosurgery device. For example, to connect an instrument with a monopolar connecting cable to an electrosurgery device, a monopolar connecting socket is used, but if an instrument with a bipolar connecting cable is to be connected to the electrosurgery device, a bipolar connecting socket must be available at the electrosurgery device. This results in a plurality of connecting sockets at the electrosurgery device with the consequence that, particularly in the hectic atmosphere of an operating room, electrosurgical instruments are often plugged into the wrong sockets. This, in turn, means that a certain amount of time passes before the incorrect insertion is noticed and the instrument is plugged into the correct connecting socket. It is even possible, as consequence of incorrect insertion, for the electrosurgical instrument to become damaged, which can have serious results for the patient being operated on.

SUMMARY

It is an object of the claimed invention to provide a simplified plug system for surgical devices that prevents incorrect connection of an electrosurgical instrument to an electrosurgery device.

In particular, this object is achieved with a plug system for surgical devices comprising a plurality of sockets into which connecting plugs of surgical instruments can be inserted, a switching matrix comprising a plurality of switches, for connecting at least one of the sockets to at least two different outputs or inputs of an electrosurgery device, and a control system having a preselection device for controlling the switching matrix such that the switching matrix connects predetermined sockets to predetermined inputs or outputs, depending on data input into the preselection device.

A key aspect of the claimed invention is that the plug system for surgical devices is used for a plurality of different electrosurgical instruments and electrosurgery devices, wherein, following input of a code, a switching matrix that identifies the electrosurgical instrument to be connected, is configured such that predetermined sockets are connected to predetermined inputs or outputs of the electrosurgery device. This reduces the number of sockets needed and enhances reliability.

In a first embodiment of the invention, the preselection device comprises a releasable connecting device, by which a connection can be made to the electrosurgical instrument for inputting data. A connecting device of this type simplifies the transmission of the data.

Preferably, the connecting device comprises a decoding socket into which a coding plug of the surgical instrument can be inserted, said coding plug being separate from the connecting plugs. The configuration of the coding plug separately from the connecting plugs enables conventional connecting plugs to continue to be used.

Preferably, the electrosurgery device is a high frequency (HF) surgery device. Particularly in the field of HF electrosurgery, the number of different instruments is large and the disclosed plug system is therefore particularly useful.

The control system preferably comprises a storage element for storing a basic configuration of a connection of sockets to inputs or outputs of the electrosurgery device. The basic configuration enables an instrument that is frequently used to be correctly connected to the electrosurgery device, even if no data is input into the preselection device.

Alternatively, in the basic configuration, all the switches of the switching matrix can be opened, ensuring that no false connections are made during the insertion of the connecting plug of the electrosurgical instrument.

In a further alternative, the storage element stores the last determined connection configuration in each case. This is particularly advantageous if a particular electrosurgical instrument is used rather frequently with the same electrosurgery device, so that if the coding plug is defective, a connection configuration suitable for the particular instrument is retrieved from the storage element.

Preferably, the data can be input manually into the preselection device. This is particularly advantageous if no coding plug is provided for a particular electrosurgical instrument or if the coding plug fails. In this case, the data which may be, for example, printed on the connecting plug, can be read and input manually into the preselection device, so that the electrosurgical instrument can be used.

BRIEF DESCRIPTION OF THE DRAWINGS

Embodiments of the invention will now be described in greater detail with reference to the drawings, in which.

DETAILED DESCRIPTION

In the following description, the same reference signs are used for the same or similarly acting parts.

Figure 1:
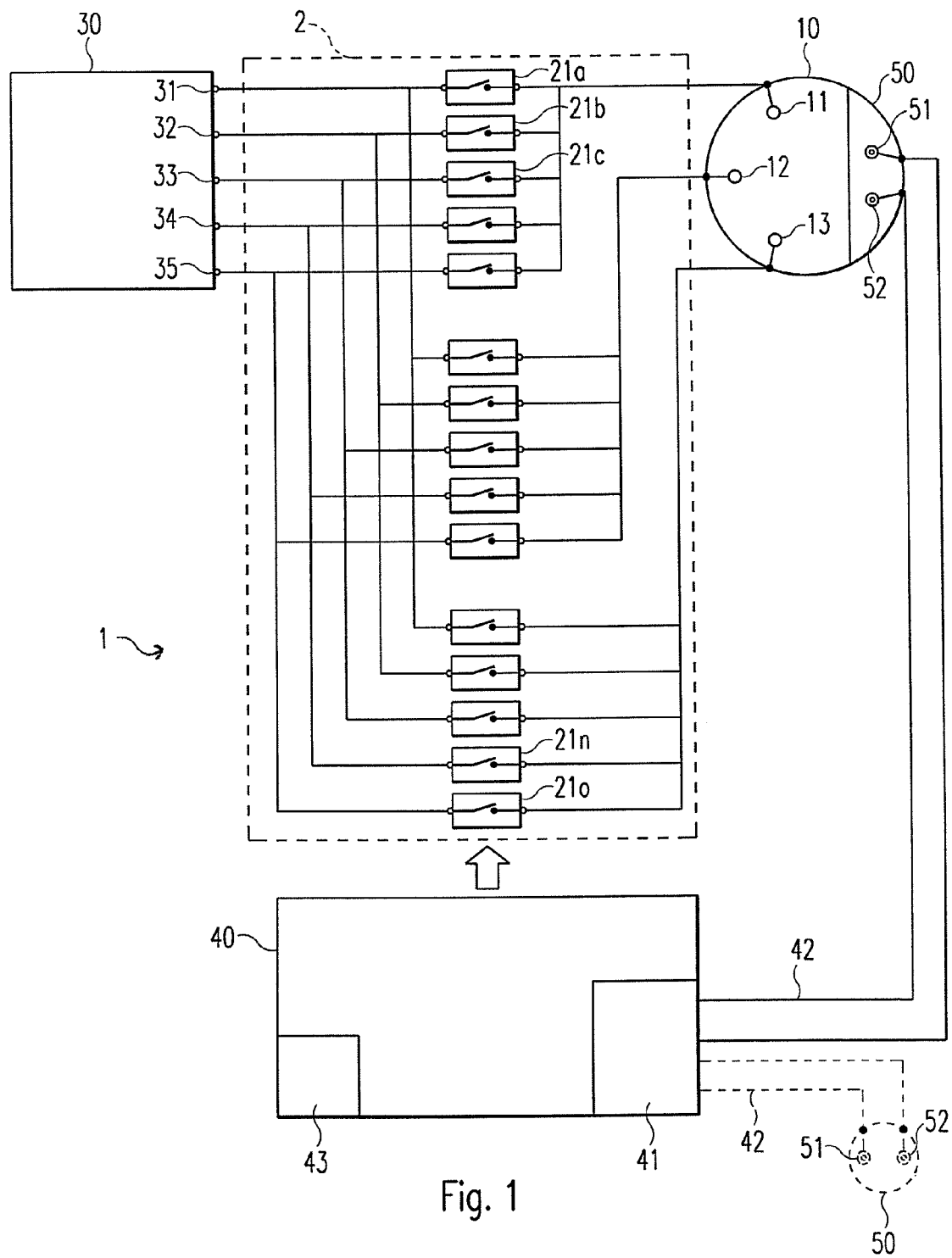
FIG. 1 shows a first embodiment of the invention.

The plug system for surgical devices 1 shown in FIG. 1 comprises a socket 10 with plug contacts 11-13, which are connected via a switching matrix 20 to inputs or outputs 31-35 of an electrosurgery device 30. A control system 40 for controlling the matrix 20 is also provided. The control system 40 analyses the data of a coding plug 60 (see FIG. 2), which is input via a decoding socket 50 into a preselection device 41, and then controls the switching matrix 20 such that switches 21a-21o of the switching matrix 20 are closed and creates an electrical connection between the plug contacts 11-13 of the socket 10 and the inputs or outputs 31-35 of the electrosurgery device 30.

Figure 2:
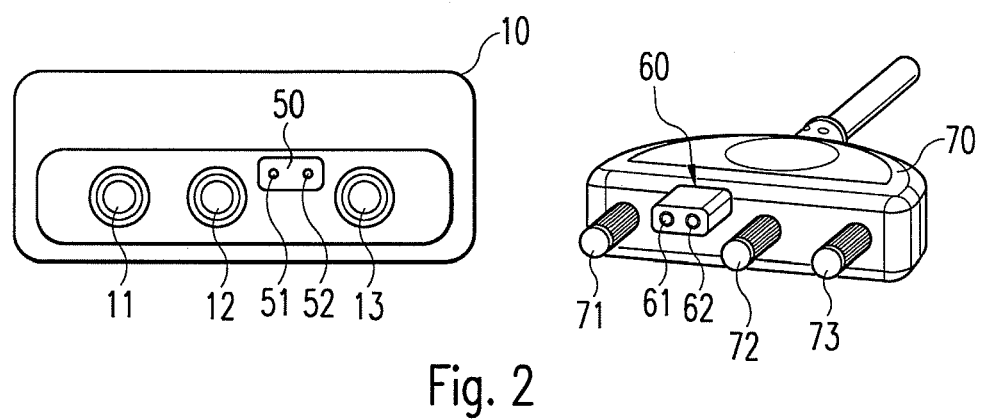
FIG. 2 shows a socket and plug arrangement for the embodiment of FIG. 1.

In the embodiment according to FIGS. 1 and 2, the plug system has a socket 10 with three plug contacts 11-13, which can be connected to five different inputs or outputs 31-35 of the electrosurgery device 30. In general, it is conceivable that an arbitrary number of sockets 10, each having an arbitrary number of plug contacts 11-13, may be connected to the inputs or outputs 31-35.

FIG. 2 shows a possible arrangement of socket 10 and decoding socket 50 on one side of the figure and connecting plug 70 and coding plug 60 on the other side. The coding plug 60 is mounted on the connecting plug 70 such that, on insertion of contact pins 71-73 of the connecting plug 70 into the plug contacts 11-13 of the socket 10, contact pins 51, 52 of the decoding socket 50, which is mounted within the socket 10, are also inserted into plug contacts 61, 62 of the coding plug 60.

In an alternative embodiment, it is also conceivable that the coding plug 60 is mounted on the electrosurgical instrument spatially separated from the connecting plug 20. Also—as shown in FIG. 1 with the dashed lines—socket 10 and decoding socket 50 can be provided separately. In an embodiment of this type, in a first step, contact pins 51, 52 of the decoding socket 50 are introduced into socket contacts 61, 62 of the coding plug 60, whereupon, the control system 40 sets the switches 21a-21o of the switching matrix 20 accordingly; in a second step, the contact pins 71, 73 of the connecting plug 70 are introduced into the socket 10. In an embodiment of this type, conventional connecting plugs 70 can be used.

The control system 40 comprises a storage element 43 for storing at least one configuration of the switching matrix 20. In the exemplary embodiment of FIGS. 1 and 2, the transmission of the data from the electrosurgical instrument to the control system 40 takes place via a wire-linked connecting device 42.

It should be appreciated that transmission of the data from the electrosurgical instrument to the control system 40 can also be performed wirelessly. For such wireless transmission of data, a coding device (not shown in the drawings), having the corresponding function to the coding plug 60, can be mounted at an arbitrary site of the electrosurgical instrument, and a decoding device, having the corresponding function to the decoding socket 50, can be mounted at an arbitrary site of the control system 40 or the electrosurgery device 30.

It is evident from the above that the embodiments of the invention concern not only a plug system for surgical devices 1, but also a method for setting a plug system for surgical devices 1.

Particularly advantageous is the use of the disclosed plug system in HF surgery, since a particularly large number of different electrosurgical instruments come into use for this type of surgery.

It should be noted that all of the parts described above are claimed as being essential to the invention both alone and in any combination, particularly the details shown in the drawings. Modifications thereof are the common practice of persons skilled in the art.

The invention claimed is:

1. A plug system for surgical devices, said system comprising:
   at least one socket having a plurality of plug contacts into which contact pins of connecting plugs of an electrosurgical instrument can be inserted;
   a switching matrix comprising a plurality of switches and for connecting at least one of the sockets to at least two different inputs or outputs of an electrosurgery device; and
   a control system having a preselection device for controlling the switching matrix such that the switching matrix connects predetermined sockets to predetermined inputs or outputs depending on data input into the preselection device, wherein
   the control system comprises a storage element for storing a basic configuration of a connection between the sockets and the inputs or outputs of the electrosurgery device, wherein the basic configuration is set if no data is entered into the preselection device, and wherein all switches are open in the basic configuration.

2. The plug system for surgical devices according to claim 1, wherein the preselection device comprises a releasable connecting device by which a connection can be made to the electrosurgical instrument to input the data.

3. The plug system for surgical devices according to claim 2, wherein the connecting device comprises at least one electrical socket.

4. The plug system for surgical devices according to claim 3, wherein a coding plug of the electrosurgical instrument can be inserted into the electrical socket, said coding plug being separate from the connecting plugs.

5. The plug system for surgical devices according to claim 1, wherein the electrosurgery device is a high frequency (HF) surgery device.

6. The plug system for surgical devices according to claim 1, wherein the storage element stores a last determined connection configuration.

7. The plug system for surgical devices according to claim 1, wherein the data can be manually input into the preselecting device.

8. A plug system for surgical devices, said system comprising:
   at least one socket having a plurality of plug contacts into which contact pins of connecting plugs of an electrosurgical instrument can be inserted;
   a switching matrix comprising a plurality of switches for connecting at least one of the sockets to at least two different inputs or outputs of high frequency (HF) electrosurgery device; and
   a control system comprising:
      a preselection device for controlling the switching matrix such that the switching matrix connects predetermined sockets to predetermined inputs or outputs depending on data input into the preselection device, said preselection device comprising a releasable connecting device by which a connection can be made to the electrosurgical instrument to input the data; and
      a storage element for storing a configuration of a connection between the sockets and the inputs or outputs of the electrosurgery device and for storing a basic configuration of a connection between the sockets and the inputs or outputs of the electrosurgery device, wherein the basic configuration is set if no data is entered into the preselection device, and wherein all switches are open in the basic configuration.

9. The plug system for surgical devices according to claim 8, wherein the connecting device comprises at least one electrical socket.

10. The plug system for surgical devices according to claim 9, wherein a coding plug of the electrosurgical instrument can be inserted into the electrical socket, said coding plug being separate from the connecting plugs.

11. The plug system for surgical devices according to claim 8, wherein the storage element stores a last determined connection configuration.

12. The plug system for surgical devices according to claim 8, wherein the data can be manually input into the preselecting device.

* * * * *

UNITED STATES PATENT AND TRADEMARK OFFICE
CERTIFICATE OF CORRECTION

PATENT NO. : 8,449,318 B2  
APPLICATION NO. : 12/809033  
DATED : May 28, 2013  
INVENTOR(S) : Beller et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 312 days.

Signed and Sealed this

Eighth Day of September, 2015

Michelle K. Lee
*Director of the United States Patent and Trademark Office*